United States Patent [19]

Floyd et al.

[11] Patent Number: 4,483,797

[45] Date of Patent: Nov. 20, 1984

[54] (S)-3-ISOCYANATO-2-OXO-1-AZETIDINE-SULFONIC ACIDS

[75] Inventors: David Floyd; Christopher M. Cimarusti, both of Pennington, N.J.

[73] Assignee: E. R. Squibb & Sons, Inc., Princeton, N.J.

[21] Appl. No.: 257,833

[22] Filed: Apr. 27, 1981

[51] Int. Cl.$^3$ ............................................. C07D 205/08
[52] U.S. Cl. ................................................. 260/239 A
[58] Field of Search .................................... 260/239 A

[56] References Cited

FOREIGN PATENT DOCUMENTS 21678 1/1981 European Pat. Off. .

79/72813 12/1980 Japan .

OTHER PUBLICATIONS

Pirkle, J. Organic Chem. 42, 2781, (1977).
Schaumann et al., Chem. Abs. 94, 174757h, (1980).

Primary Examiner—Mark L. Berch
Attorney, Agent, or Firm—Lawrence S. Levinson; Donald J. Barrack

[57] ABSTRACT

3-Isocyanato-2-oxo-1-azetidinesulfonic acid salts are novel intermediates which are useful in processes for the preparation of 3-amino-2-oxo-1-azetidinesulfonic acid salts and 3-acylamino-2-oxo-1-azetidinesulfonic acid salts.

7 Claims, No Drawings

(S)-3-ISOCYANATO-2-OXO-1-AZETIDINESULFONIC ACIDS

RELATED APPLICATION

U.S. patent application Ser. No. 226,562, filed Jan. 19, 1981, discloses novel β-lactam antibiotics. These products are zwitterions or salts of a β-lactam having a sulfonic acid substituent —SO₃H in the 1-position and an acylamino substituent in the 3-position.

BRIEF DESCRIPTION OF THE INVENTION

This invention is directed to a process for the preparation of certain 3-amino-2-oxo-1-azetidinesulfonic acid salts and certain 3-acylamino-2-oxo-1-azetidinesulfonic acid salts. The process of this invention may be represented diagramatically as follows:

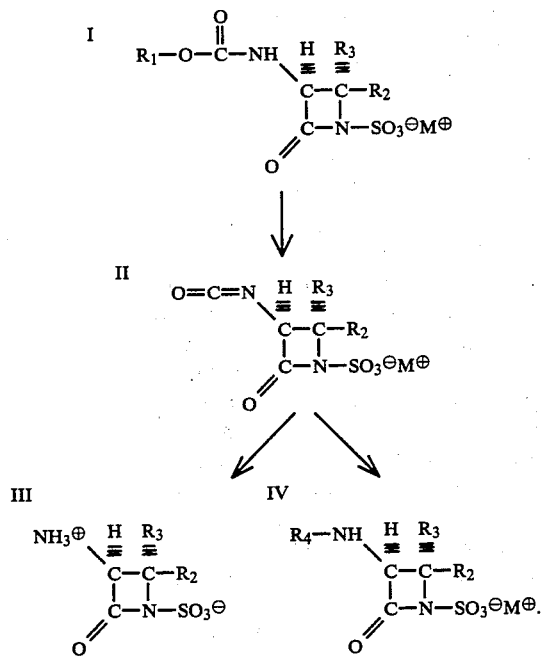

The 3-isocyanato-2-oxo-1-azetidinesulfonic acid salts of formula II are novel intermediates, and as such, constitute an integral part of this invention.

In formulas I, II, III and IV, and throughout the specification, the symbols are as defined below.

$R_1$ is alkyl, aryl, or arylalkyl;
$R_2$ and $R_3$ are the same or different and each is hydrogen or alkyl;
$R_4$ is acyl; and
$M^\oplus$ is hydrogen or a cation.

Listed below are definitions of various terms used herein. These definitions apply to the terms as they are used throughout the specification (unless they are otherwise limited in specific instances) either individually or as part of a larger group.

The term "alkyl" refers to both straight and branched chain groups. Those groups having 1 to 10 carbon atoms are preferred.

The term "halogen" refers to fluorine, chlorine, bromine and iodine.

The term "aryl" refers to phenyl or substituted phenyl.

The term "substituted phenyl" refers to a phenyl group substituted with 1, 2 or 3 halogen, trifluoromethyl, alkyl (of 1 to 4 carbon atoms), or alkoxy (of 1 to 4 carbon atoms) groups.

The term "acyl" includes all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, British Pat. No. 1,348,894, published Mar. 27, 1974, and U.S. patent application Ser. No. 226,562, filed Jan. 19, 1981. The portions of these references describing various acyl groups are incorporated herein by reference.

The term "cation", as used throughout the specification, refers to any positively charged atom or group of atoms. The "—SO₃⊖M⊕" substituent on the nitrogen atom of the β-lactams prepared by the process of this invention encompasses all sulfonic acid salts (including inner salts; i.e., M⊕ is hydrogen). Pharmaceutically acceptable salts are preferred for the antibiotics of formula IV, while lipophilic salts are particularly useful in the process of this invention. The cationic portion of the —SO₃⊖M⊕ group can be obtained from either organic or inorganic bases. Such cationic portion includes, but is not limited to, the following ions: ammonium; substituted ammonium, such as alkylammonium (e.g., tetra-n-butylammonium, referred to hereinafter as tetrabutylammonium); alkali metal, such as lithium, sodium and potassium; alkaline earth metal, such as calcium and magnesium; pyridinium; dicyclohexylammonium; hydrabaminium; benzathinium; N-methyl-D-glucaminium.

DETAILED DESCRIPTION OF THE INVENTION

The process of this invention yields a 3-amino-2-oxo-1-azetidinesulfonic acid of formula III or a 3-acylamino-2-oxo-1-azetidinesulfonic acid salt of formula IV. As described in U.S. patent application Ser. No. 226,562, filed Jan. 19, 1981, a compound of formula III can be reacted with a carboxylic acid, or corresponding carboxylic acid halide or carboxylic acid anhydride, to yield antibiotics having the formula

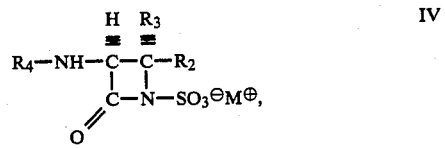

wherein M⊕ is hydrogen or a cation. The reaction with a carboxylic acid proceeds most readily in the presence of a carbodiimide such as dicyclohexylcarbodiimide and a substance capable of forming an active ester in situ such as N-hydroxybenzotriazole. In those instances when the acyl group contains reactive functionality (such as amino or carboxyl groups) it may be necessary to first protect those functional groups, then carry out the acylation reaction, and finally deprotect the resulting product. The β-lactam antibiotics of formula IV can be used as agents to combat bacterial infections (including urinary tract infections and respiratory infections) in mammalian species, such as domesticated animals and humans. It is further disclosed that for combating bacterial infections in mammals a compound of formula I can be administered to a mammal in need thereof in an amount of about 1.4 mg/kg/day to about 350 mg/kg/day, preferably about 14 mg/kg/day to about 100 mg/kg/day.

The starting material used in the process of this invention is a β-lactam having the formula

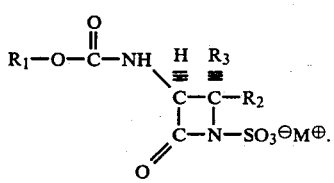

Compounds of formula I are disclosed in U.S. patent application Ser. No. 226,562, filed Jan. 19, 1981.

Reaction of a compound of formula I with a silyl halide, e.g., silicon tetrachloride, trichlorosilane, trimethyl chlorosilane, or trimethoxy chlorosilane, in the presence of an organic base, e.g., triethylamine or pyridine, yields the corresponding β-lactam having the formula

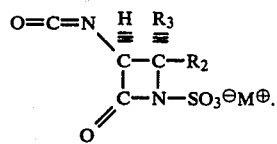

Conversion of a 3-isocyanato-2-oxo-1-azetidinesulfonic acid salt to the corresponding 3-amino-2-oxo-1-azetidinesulfonic acid inner salt (M⊕ is hydrogen) having the formula

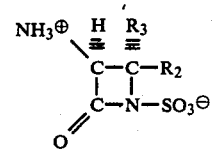

can be accomplished by acid hydrolysis. Treatment of a compound of formula II with an acid such as formic acid effects the desired conversion.

Alternatively, a 3-isocyanato-2-oxo-1-azetidinesulfonic salt of formula II can be acylated to yield a β-lactam having the formula

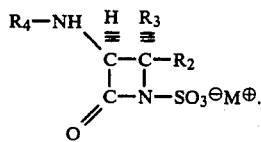

Acylation is readily accomplished by heating a compound of formula II with the appropriate carboxylic acid in an inert solvent. A catalyst, such as an organic base (e.g., triethylamine) can be added to the reaction.

The following examples are specific embodiments of this invention.

EXAMPLE 1

(3S-trans)-3-Amino-4-methyl-2-oxo-1-azetidinesulfonic acid, inner salt

A solution of 479 mg (0.001 mole) of (3S-trans)-3-methoxycarbonylamino-4-methyl-2-oxo-1-azetidinesulfonic acid, tetrabutylammonium salt in 10 ml of dichloromethane is treated with 139 μl of triethylamine and 112 μl of trichlorosilane. The resulting solution is refluxed for 3 hours and cooled to 0° C. Triethylamine (139 μl) and 0.5 ml of water are added, and the solution is stirred overnight. The resulting slurry is diluted with 20 ml of formic acid, stirred for 1 hour, and the solid filtered to give 117 mg of (3S-trans)-3-amino-4-methyl-2-oxo-1-azetidinesulfonic acid, inner salt.

EXAMPLE 2

(3S-trans)-3-Amino-4-methyl-2-oxo-1-azetidinesulfonic acid, inner salt

A solution of 531 mg (0.001 mole) of (3S-trans)-4-methyl-2-oxo-3-(phenyloxycarbonylamino)-1-azetidinesulfonic acid, tetrabutylammonium salt in 10 ml of 1,2-dichloroethane is treated with 278 μl of triethylamine and 250 μl of trimethyl chlorosilane and the solution refluxed for 75 minutes. An aliquot of the reaction mixture shows intense IR absorption of 2270 cm$^{-1}$ (indicative of the isocyanate group) and almost complete disappearance of the 1745 cm$^{-1}$ band (for the urethane function) in addition to a strong absorption at 1770 cm$^{-1}$ (β-lactam). The solution is refluxed for 20 hours (no change in IR), cooled to 0° C., and 2 ml of 88% formic acid is added. After 2.5 hours at room temperature the slurry is filtered to give 118 mg of (3S-trans)-3-amino-4-methyl-2-oxo-1-azetidinesulfonic acid, inner salt.

EXAMPLE 3

(3S-trans)-4-Methyl-2-oxo-3-(phenylacetylamino)-1-azetidinesulfonic acid, tetrabutylammonium salt A solution of 531 mg (0.001 mole) of (3S-trans)-4-methyl-2-oxo-3-(phenyloxycarbonylamino)-1-azetidinesulfonic acid, tetrabutylammonium salt, in 15 ml of 1,2-dichloroethane is refluxed for 90 minutes with 278 μl of triethylamine and 250 μl of trimethylchlorosilane. After distillation of 5 ml of solvent, a solution of 136 mg of phenylacetic acid and 140 μl of triethylamine in 1 ml of dimethylformamide is added and the mixture is refluxed for 2 hours. The reaction mixture is poured into water and extracted into dichloromethane. After washing with saturated sodium bicarbonate solution, the organic layer is dried and evaporated. Trituration with ether gives 239 mg of (3S-trans)-4-methyl-2-oxo-3-(phenylacetylamino)-1-azetidinesulfonic acid, tetrabutylammonium salt.

What is claimed is:
1. A β-lactam having the formula

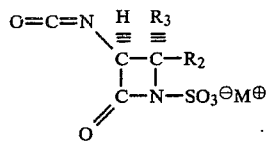

wherein $R_2$ and $R_3$ are the same or different and each is hydrogen or alkyl and $M^\oplus$ is hydrogen or a cation.

2. A β-lactam in accordance with claim 1 wherein $R_2$ is hydrogen and $R_3$ is methyl.

3. A β-lactam in accordance with claim 1 wherein $R_2$ is methyl and $R_3$ is hydrogen.

4. A β-lactam in accordance with claim 1 wherein $R_2$ and $R_3$ are each hydrogen.

5. A β-lactam in accordance with claim 1 wherein $M^\oplus$ is tetrabutylammonium.

6. A β-lactam in accordance with claim 1 wherein $M^\oplus$ is hydrogen.

7. A β-lactam in accordance with claim 1, said β-lactam being a lipophilic β-lactam salt.

* * * * *